United States Patent [19]

Crainich

[11] Patent Number: 5,549,637

[45] Date of Patent: Aug. 27, 1996

[54] ARTICULATED MEDICAL INSTRUMENT

[76] Inventor: Lawrence Crainich, P.O. Box. 996 Ceda Rd., Charlestown, N.H. 03603

[21] Appl. No.: 337,563

[22] Filed: Nov. 10, 1994

[51] Int. Cl.$^6$ .................................................. A61B 17/00
[52] U.S. Cl. .......................................... 606/207; 606/170
[58] Field of Search .............................. 606/51, 52, 139, 606/174, 205–211; 128/751–755, 4, 6

[56] References Cited

U.S. PATENT DOCUMENTS

| | | | |
|---|---|---|---|
| 4,483,562 | 11/1984 | Schoolman | 606/174 |
| 4,880,015 | 11/1989 | Nierman | 128/751 |
| 5,209,747 | 5/1993 | Knoepfler | 606/205 |
| 5,374,277 | 12/1994 | Hassler | 606/207 |

Primary Examiner—Gary Jackson
Assistant Examiner—William Lewis
Attorney, Agent, or Firm—Bachman & LaPointe, P.C.

[57] ABSTRACT

A medical instrument includes a handle; an elongate body member having a first end and a second end and at least one joint disposed therebetween dividing the body member into a plurality of segments including a first segment and a second segment, the first segment being connected to the handle and the second segment terminating in a tool head receiver; a member for pivoting the second segment relative to the first segment at the at least one joint between; a member for rotating the tool head receiver relative to the body member; and a member for rotating the body member relative to the handle.

39 Claims, 7 Drawing Sheets

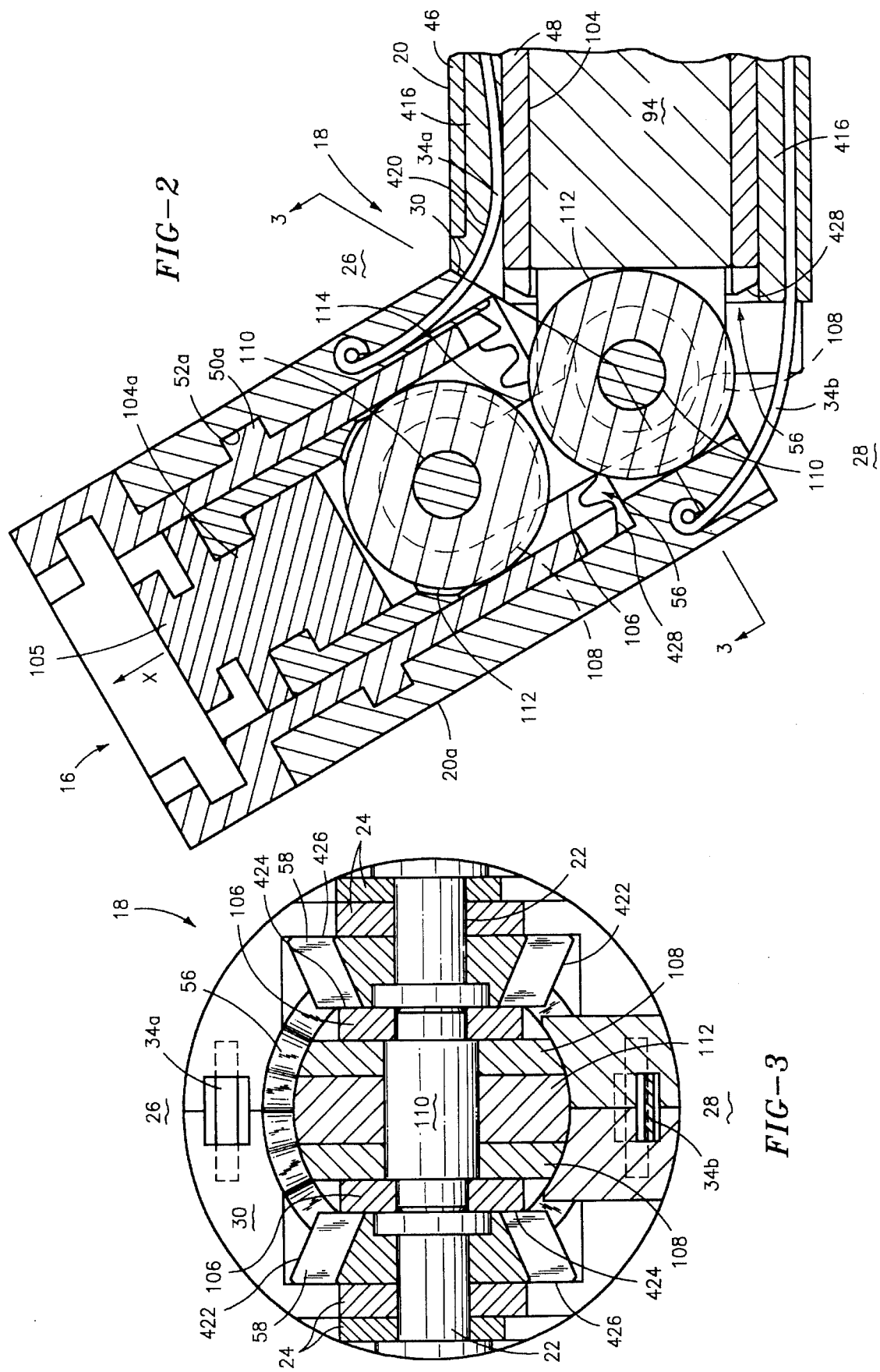

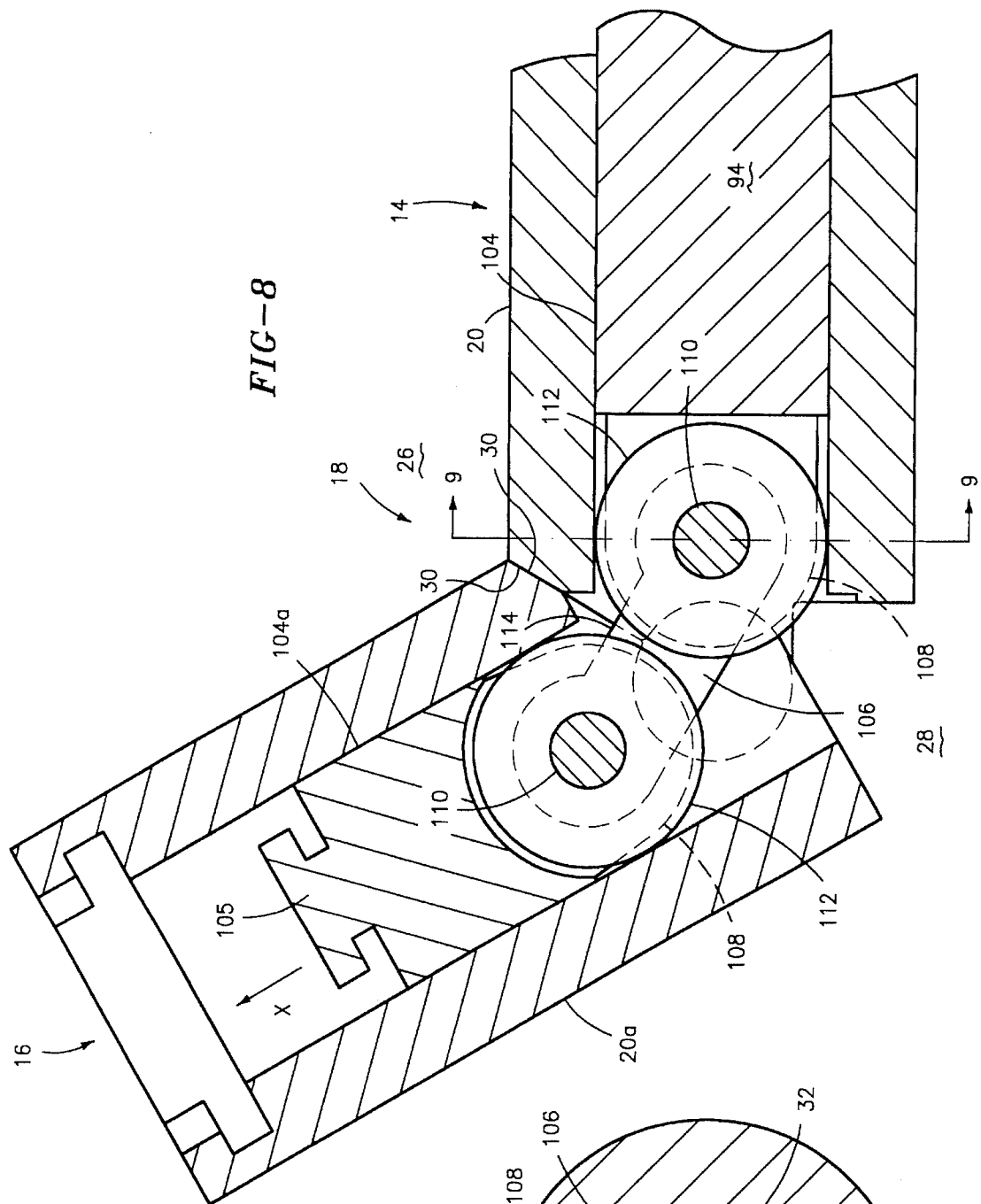

ARTICULATED MEDICAL INSTRUMENT

BACKGROUND OF THE INVENTION

The invention relates to a medical instrument and, particularly, to a medical instrument wherein a tool head is mounted to a substantially elongate body member.

Numerous medical instruments are known for use in laparoscopic and other surgical procedures wherein tools are inserted into or positioned at a desired location of the body of a patient, typically through a cannula or similar device.

Once inserted through the cannula, conventional devices have limited versatility in terms of mobility of the tool head.

It is the primary object of the present invention to provide a medical instrument wherein the tool head may be pivoted, rotated with the tool body, and twirled relative to the tool body so as to provide enhanced versatility.

It is a further object of the invention to provide such a medical instrument wherein the tool head is releasable and exchangeable whereby the instrument is useful in a wide range of medical and surgical procedures or operations.

It is a still further object of the invention to provide a medical instrument which allows procedures to be carried out through a cannula which procedures would conventionally require a larger incision for proper access.

Other objects and advantages will appear hereinbelow.

SUMMARY OF THE INVENTION

The foregoing objects and advantages are readily attained by the present invention.

According to the invention, an articulated medical instrument is disclosed which comprises a handle; an elongate body member having a first end and a second end and at least one joint disposed therebetween dividing the body member into a plurality of segments including a first segment and a second segment, the first segment being connected to the handle and the second segment terminating in a tool head receiving means; means for pivoting the second segment relative to the first segment at the at least one joint; means for rotating the tool head receiving means relative to the body member; and means for rotating the body member relative to the handle.

In accordance with the foregoing, an extraordinarily versatile instrument is provided which greatly expands the locations which can be accessed or treated as desired.

According to a preferred embodiment of the invention, the body member is provided with three joints each pivotable up to about 60° whereby the tool head receiver is pivotable up to a total of 180° relative to the straight position thereof.

In further accordance with the invention, the medical instrument preferably includes a push member longitudinally slidably disposed within the inner portion of the segments of the body member and having a first end associated with the handle, a second end associated with the tool head receiving means, and means for hinging the push member arranged substantially adjacent to the at least one joint whereby the push member is pivotable with the body member and rotatable with the body member relative to the handle.

BRIEF DESCRIPTION OF THE DRAWINGS

A detailed description of preferred embodiments of the invention follows, with reference to the attached drawings wherein:

FIG. 2 is a sectional view of a joint of the medical instrument according to the invention;

FIG. 3 is a cross-section taken along the lines 3—3 of FIG. 2;

FIG. 8 is a simplified sectional view of the push member structure of the joint of FIG. 2; and FIG. 9 is a cross-section taken along the lines 9—9 of FIG. 8.

DETAILED DESCRIPTION

The invention relates to an articulated medical instrument having a body member for supporting an instrument tool head and having at least one joint structure in the body member whereby the tool head of the instrument can be pivoted, rotated with the body member, and twirled relative to the body member so as to provide an extraordinarily versatile device.

Figure 1:
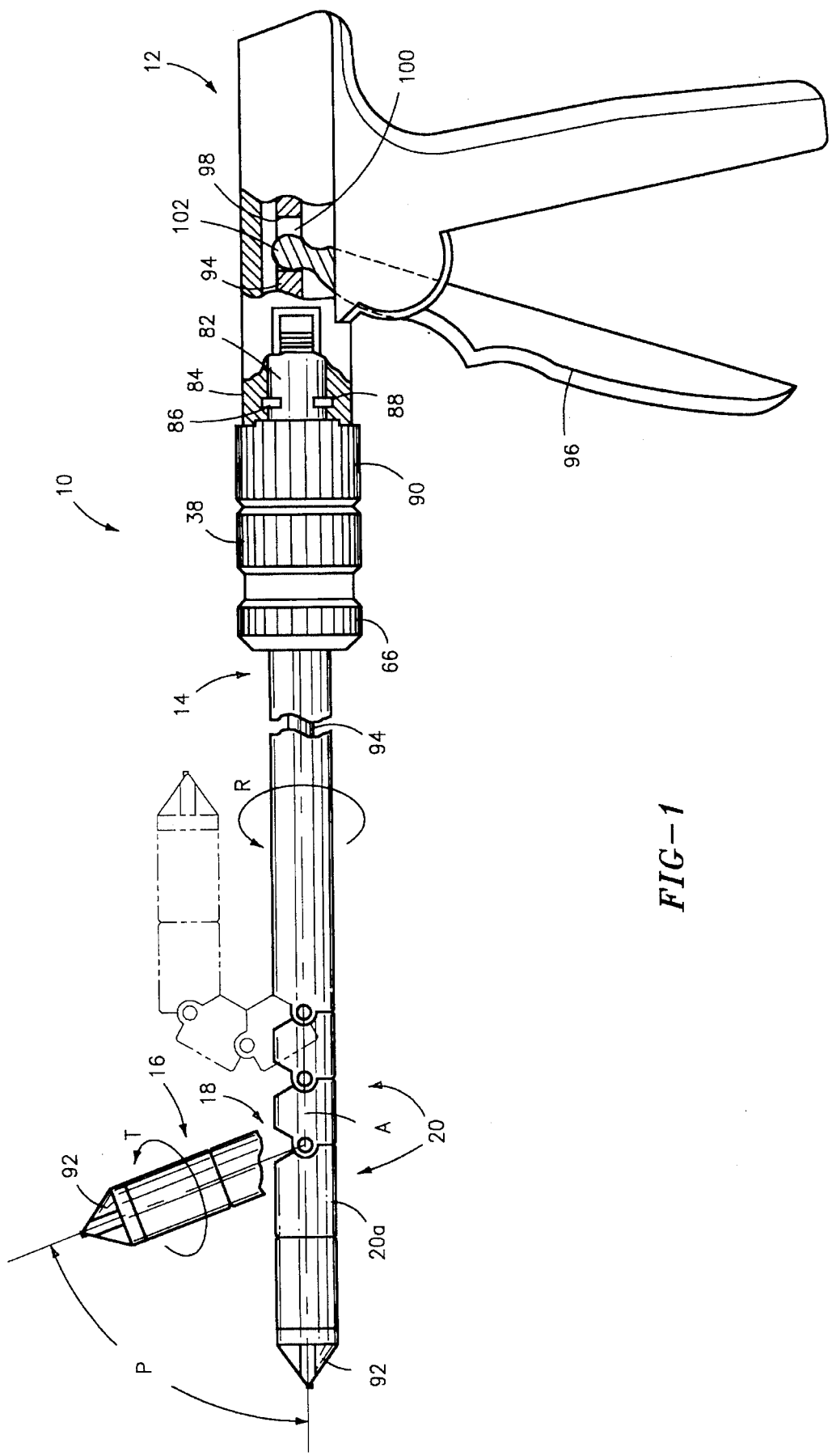
FIG. 1 is a side view, partially broken away, of an articulated medical instrument according to the invention.

FIG. 1 illustrates a side view of a medical instrument 10 according to the invention having a handle portion 12, and an elongate substantially tubular body member 14 connected to the handle 12 at one end and terminating in a tool head coupler 16 at the other end. According to the invention, at least one joint structure 18 is disposed along body member 14 whereby tool head coupler 16 is pivotable, around a joint 18, relative to the longitudinal axis A of the remaining portion of the body member as shown by arrow P. In further accordance with the invention, joint structure 18 joins inner structure of body member 14 so that tool head coupler 16 is rotatable or twirlable relative to body member 14 as shown by arrow T, and further so that body member 14 with tool head coupler 16 is rotatable relative to handle 12 as shown by arrow R. According to the invention, body member 14 is preferably provided with three joint structures 18 as shown in FIG. 1 which, as will be described below, advantageously allow for 180° pivot of tool head coupler 11 relative to body member 14.

According to the invention, one or more joints 18 are disposed along the length of body member 14 to articulate and divide body member 14 into segments 20 which are pivotable relative to each other. FIGS. 2 and 3 are detailed sectional views of a joint structure 18 according to the invention which advantageously provides for the desired pivot, twirl and rotation in accordance with the invention. FIGS. 4, 6, 8 and 9 are simplified sections of joint 18 illustrating various portions of the structure of joint 18 for providing the desired pivot, rotation and twirl.

Figure 4:
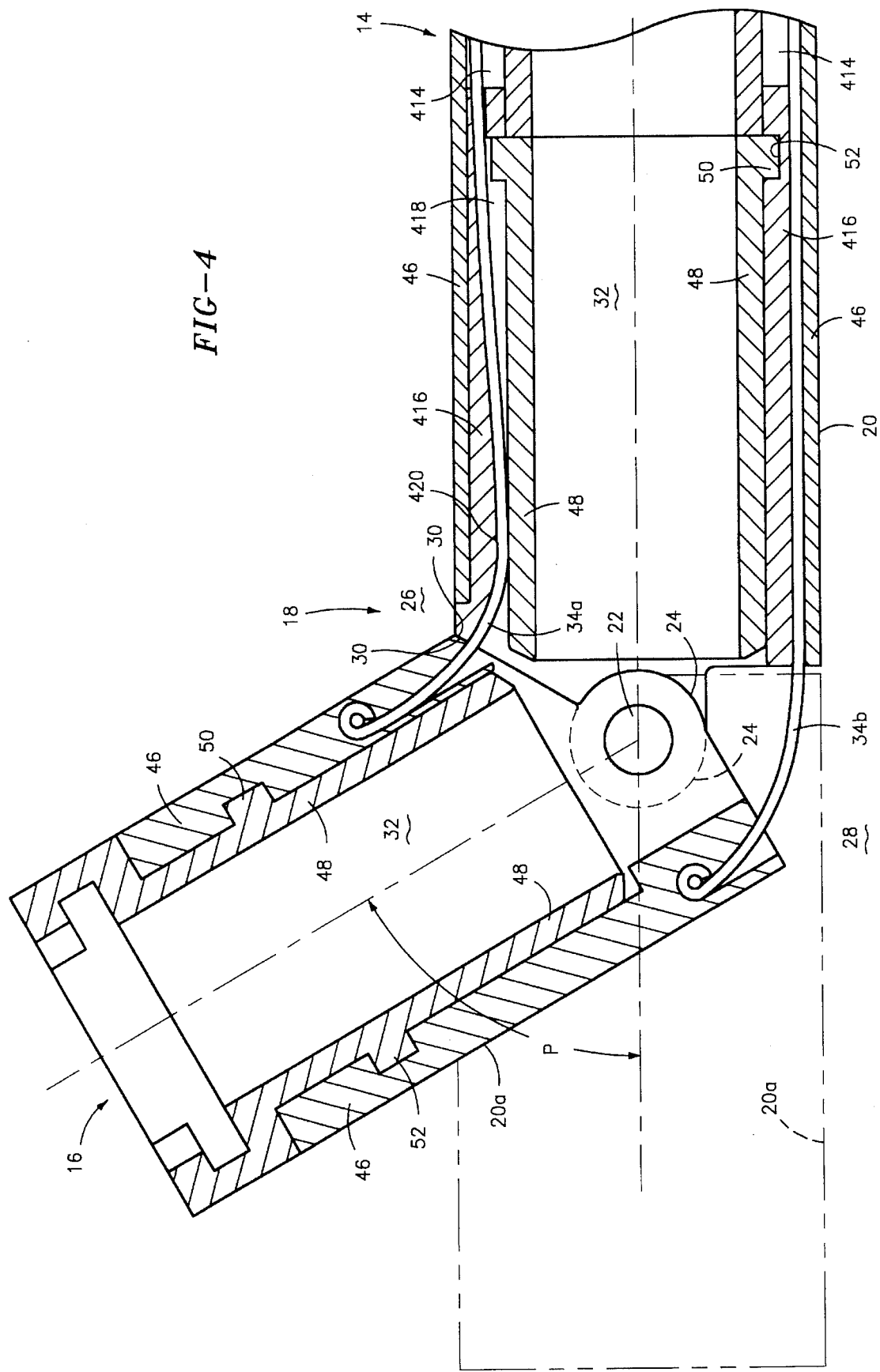
FIG. 4 is a simplified sectional view of the pivoting structure of the joint of FIG. 2.

Referring to FIG. 4, a simplified section of joint 18 is provided so as to illustrate the structure according to the invention for providing pivot at joint 18. According to the invention, segments 20 of body member 14 are preferably pivotably connected at joints 18. Segments 20 preferably have bearings 24 pivotably disposed on an axle 22 so as to provide the desired pivotable connection at joint 18. Of course, other types of hinge or joint connections are known in the art and could suitably be used according to the invention.

Joint 18 renders segments 20 pivotable relative to one another between a substantially straight position (outlined in dashed lines in FIG. 4) and a pivoted position as shown in FIG. 4. As illustrated in the drawing, joint 18 at which segments 20 are connected has a pivotally inner side 26 and a pivotally outer side 28. As shown, pivot around joint 18 is toward pivotally inner side 26 and away from pivotally outer side 28. To facilitate the desired pivot, segments 20 preferably have an angled back portion 30 as shown to allow for the full desired range of pivot. Of course, only one segment at each joint 18 needs to have an angled back portion 30, but it is preferable to provide both segments 20 with angled back portions 30 to provide a more versatile and stable device. Further, providing angled back portions 30 on both segments 20 helps to provide modular segments which may be interchangeably connected at joints 18 in any desired number.

According to the invention, the pivot providing structure of joint 18, namely axle 22 and bearings 24, are preferably positioned substantially in close proximity to the wall of segments 20 of body member 14. In accordance with the invention, bearings 24 may suitably be extensions from the wall of segments 20 to provide the desired "side hinging" at joint 18. Side hinging at joint 18 is desirable in accordance with the invention so as to keep inner space 32 of body member 14 substantially unobstructed. As will be discussed below in detail, the preferred side hinging of joint 18 prevents joint 18 from interfering with a push rod structure to be disposed within body member 14 for operating a tool to be disposed on tool head coupler 16.

Pivot around joint 18 is preferably provided and controlled by band members 34 slidably positioned within the side wall of segments 20 of body member 14. Bands 34 are preferably connected at one end to the distal or last segment 20a of body member 14 which terminates in tool head coupler 16, and at the other end to a control member for sliding or tensioning bands 34 (shown and described below with reference to FIGS. 5 and 5A). In this manner, longitudinal sliding or tensioning of bands 34 relative to body member 14 provides the desired pivot of segment 20a around joint 18.

As shown in FIG. 4, two bands 34a, 34b are preferably provided, one (band 34a) positioned on pivotally inner side 26 of body member 14, and the other (band 34b) positioned on pivotally outer side 28. Bands 34 are preferably flexible to provide for pivot or bending of the bands 34 at joint 18. In accordance with the invention, sliding of band 34a toward handle 12, or "tensioning" of band 34a, results in pivot of segment 20a relative to segment 20 to the pivoted position of FIG. 4. Sliding of band 34b toward handle 14, or "tensioning" of band 34b, results in pivot of segment 20a relative to segment 20 back toward the substantially straight position outlined in dashed lines in FIG. 4. According to the invention, operation of bands 34a, 34b is preferably substantially simultaneous, that is, "tensioning" of band 34a is preferably accompanied by sliding of band 34b away from handle 12, or "relaxing" of band 34b, and vice versa.

It should be noted that band members 34, in accordance with the invention, may suitably be wires, cables and the like, or any other elongate connection member which preferably is at least partially flexible.

Figure 5:
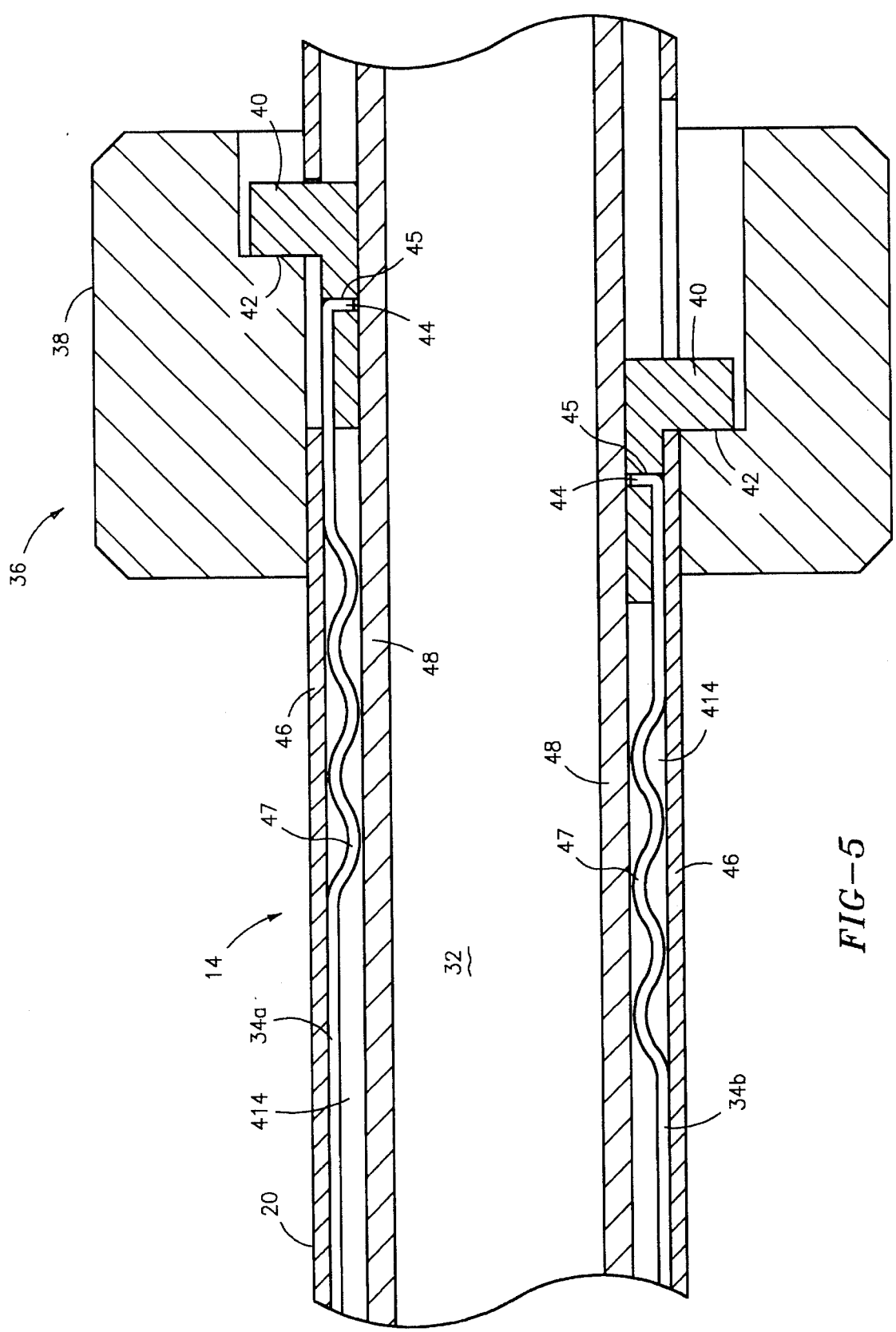
FIG. 5 is a sectional view of a pivot control member according to the invention.
Figure 5A:
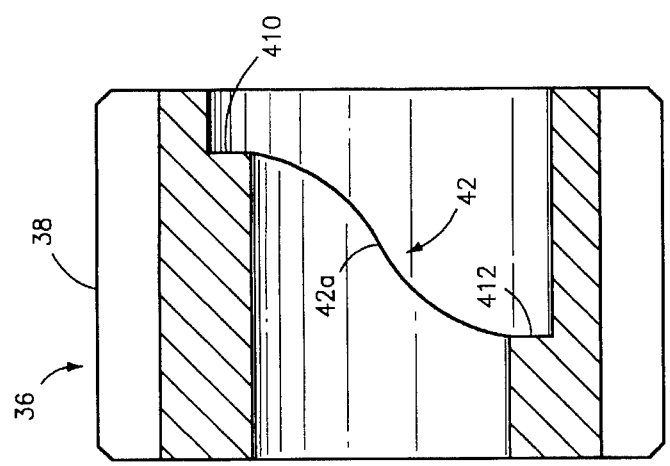
FIG. 5A is a sectional view of an element of the pivot control member of FIG. 5.

Referring now to FIG. 5, a control member 36 is illustrated for providing the desired alternate "tensioning" and "relaxing" of bands 34a and 34b in accordance with the invention. As shown, control member 36 is preferably a collar member 38 rotatably mounted around body member 14, preferably in close proximity to handle 12, (as best shown in FIG. 1). Bands 34a, 34b preferably extend through body member 14 and are associated with collar 38 for example through retainers 40 contacting an inner cam surface 42 of collar 38 as shown. Referring to FIG. 5A, collar 38 preferably has a cam surface 42 having two cam segments sloping helically in opposite directions to provide simultaneous tensioning and releasing of bands 34a, 34b when collar 38 is rotated, all as desired in accordance with the invention. One full cam segment 42a of cam surface 42 is illustrated in FIG. 5A. As shown, cam segment 42a preferably has a "high" point 410 at one end corresponding to a fully tensioned position of band 34a and a "low" point 412 at the other end corresponding to a fully relaxed position of band 34a. High point 410 and low point 412 are preferably connected by a smooth helical surface as shown so as to provide smooth transition of retainer 40 and band 34a between the tensioned and relaxed position. Each cam segment provides a path followed by one band 34a, 34b during rotation of collar 38. Thus, the segment not shown in FIG. 5A in accordance with the invention is a mirror image to segment 42a and connects high point 410 and low point 412 along the sectioned away half of collar 38. Thus, rotation of collar 38 through 180° provides full and simultaneous transition of bands 34a, 34b between the tensioned and relaxed positions.

As illustrated in FIG. 5, bands 34a, 34b preferably have an angled end 44 which is preferably engaged with retainers 40 for example in notch 45. Rotation of collar 38 causes cam surface 42 to longitudinally displace retainers 40 thereby providing the desired sliding of bands 34a, 34b. In accordance with the invention, bands 34a, 34b may preferably have convolutions 47 or bends disposed therein to provide a spring-like action to bands 34a, 34b. In this way, bands 34a, 34b are maintained physically in tension as they are being "tensioned" or "relaxed" so as to prevent undesirable free play of segments 20 relative to each other.

It should be noted, of course, that numerous other means could be used in accordance with the invention to provide the desired pivot of segments 20 around joints 18.

It should also be noted that a plurality of joints 18 may be disposed along body member 14 (as illustrated in FIG. 1) in accordance with the invention so as to provide a greater overall degree of pivot from a straight position. According to a preferred embodiment of the invention, three joints 18 may be provided along body member 14, each pivotable up to an angle of about 60 degrees. Thus, in accordance with the invention, tool head 16 may be pivoted through an infinite range of pivot between a substantially straight position (0 degrees) and about a 180 degree pivot relative to the straight position.

Of course, any desired number of joints 18 pivotable up to any desired angle could be employed in accordance with the invention so as to provide a particular desired pivotability.

Figure 6:
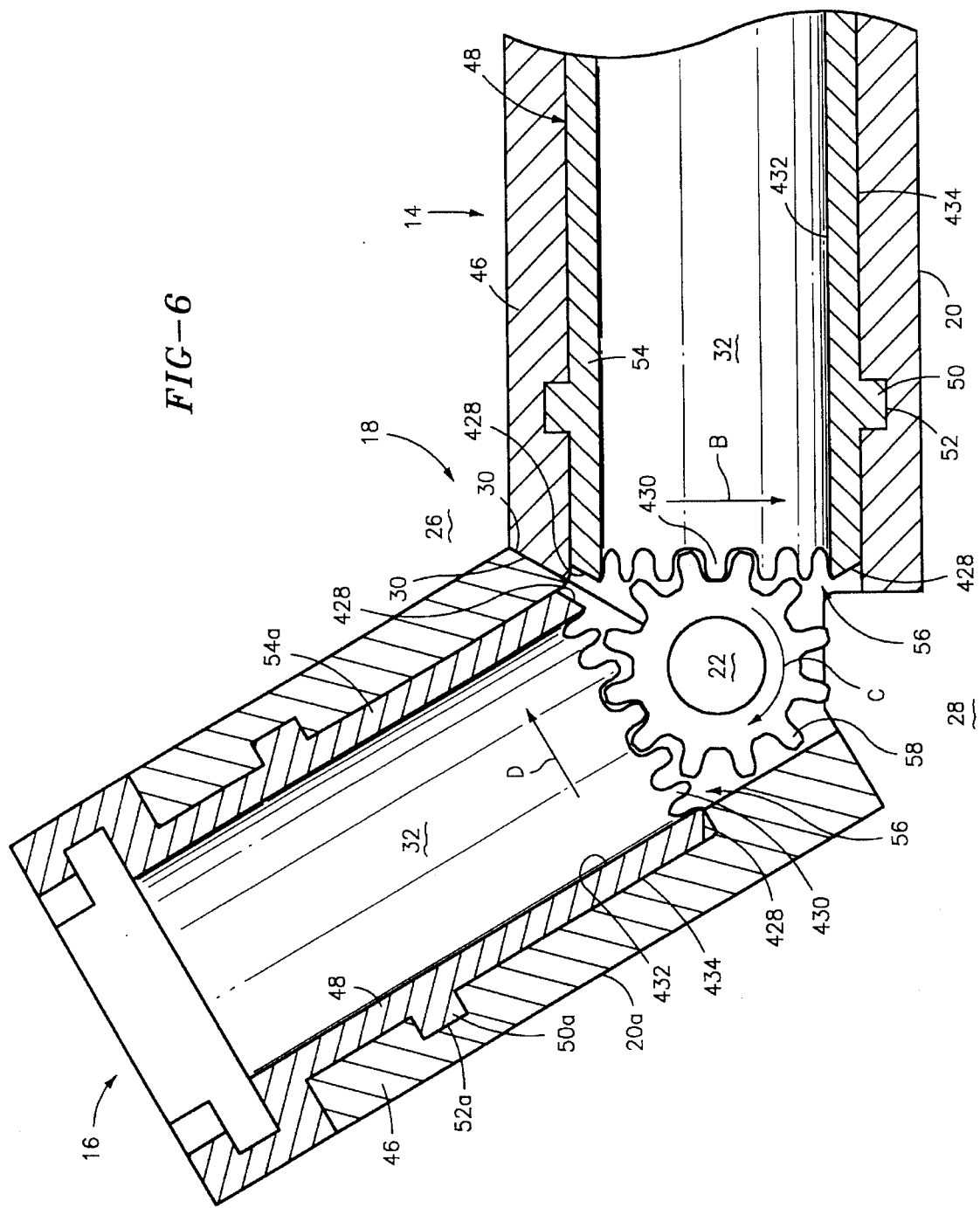
FIG. 6 is a simplified sectional view of the twirling structure of the joint of FIG. 2.

As set forth above, medical instrument 10 and joint structure 18 according to the invention also provide for twirling (Arrow T—FIG. 1) or rotation of tool head coupler 16 relative to body member 14. FIG. 6 illustrates a simplified version of joint 18 showing the elements and structure according to the invention for providing the desired twirling of tool head coupler 16 relative to body member 14.

According to the invention, body member 14 is a substantially elongate tubular member having an outer tubular portion 46 and an inner tubular portion 48 which is rotatably mounted within outer tubular portion 46. Inner tubular portion 48 preferably terminates in tool head coupler 16, preferably accessible or projecting from segment 20a, so that rotation of inner portion 48 relative to outer portion 46 provides the desired twirl or rotation of tool head coupler 16.

As shown in FIGS. 2–5, bands 34a, 34b are preferably positioned between outer portion 46 and inner portion 48. As best shown in FIG. 4, outer portion 46 and inner portion 48 define an annular space 414 therebetween, and bands 34a, 34b are positioned within space 414. According to the invention, a central tubular portion 416 is preferably disposed within outer portion 46, preferably at end portions thereof as shown, so as to properly space inner portion 48 relative to outer portion 46. Central portion 416 is preferably fixedly mounted within outer portion 46, and has channels or tracks 418 through which bands 34a, 34b are slidably disposed. Tracks 418 may preferably have rounded surfaces 420, as shown, in the area adjacent to joints 18 so as to reduce the wear on bands 34a, 34b when body member 14 is pivoted. Central portion 416 may also preferably be provided with tracks 52 on an inner surface thereof, and inner portion 48 may preferably have tabs 50 on an outer surface thereof. Tabs 50 are preferably sized to slidably fit within tracks 52 of central portion 416 so that inner portion 48 is rotatably held within central portion 416 and outer portion 46 and is held against longitudinal sliding relative to central portion 416.

Of course, any other suitable structure could be used in accordance with the invention to rotatably fix inner portion 48 in place within outer portion 46.

It should also be noted that segment 54a of inner portion 48 is preferably longitudinally held within outer portion 46 of segment 20a. This may readily be accomplished in accordance with the invention by providing tabs 50a on inner segment 54a and tracks 52a on segment 20a for receiving tabs 50a whereby segment 54a is rotatable but longitudinally held within segment 20a as desired.

Referring now to FIG. 6, joint 18 according to the invention provides for rotation of inner portion 48 relative to outer portion 46 regardless of the angle of pivot of joint 18.

According to the invention, joint 18 includes structure for pivotably joining inner portions 48 of segments 20 so that pivot of segments 20 does not interrupt the continuity of rotation of inner portion 48 relative to outer portion 46. As shown in FIG. 6, inner portion 48 is preferably divided into inner segments 54 which are pivotally connected by gear connections positioned at joint 18. An end inner segment 54a of inner portion 48 preferably terminates in tool head coupler 16 as set forth above. As shown, each inner segment 54 preferably ends or terminates in a toothed or bevel gear end 56 which, according to the invention, is engaged by an additional bevel gear 58 which serves to transmit rotation of one inner segment 54 to the next inner segment 54a. As shown in the drawings, gear end 56 is preferably a plurality or series of teeth spaced around and extending longitudinally from one or both ends of each segment 54. In this regard, last segment 54a obviously needs only one gear end 56. Depending upon the number of joints 18 to be used, interior segments 54 would of course terminate in gear ends 56 at both ends thereof. According to the invention, bevel gear 58 is mounted substantially coaxially with joint 18 so as to rotate around substantially the same axis as that about which joint 18 pivots. In this manner, advantageously, gear 58 stays engaged with adjacent bevel gear ends 56 of inner segments 54 when segments 20 of body member 14 are pivoted at joint 18.

Bevel gear 58 and bevel gear ends 56 preferably have beveled gear surfaces as set forth above so that gear 58 and gear ends 56 engage smoothly regardless of the angle of pivot of joint 18. Gear 58 preferably has a beveled surface 422 (see FIG. 3) which is beveled radially inwardly so as to increase the radius of gear 58 as measured from the inner edge 424 to the outer edge 426 of gear 58.

Gear ends 56 preferably also have beveled surfaces 428 (see for example FIG. 6) which are beveled radially outwardly so as to shorten the length of teeth 430 of gear ends 56 as measured from the inner surface 432 to the outer surface 434 of gear end 56. In this way, beveled surfaces 428 are advantageously sloped so as to mesh or mate with beveled surfaces 422 of gear 58, thereby providing smooth engagement of gear 58 and ends 56 as desired.

As best illustrated in FIG. 3, each joint 18 may include two bevel gears 58 spaced laterally to each side of inner segments 54 so as to enhance stability of the device. Further, bevel gears 58 may suitably be rotatably mounted on the same axle member 22 as bearing members 24 of joint 18. Returning to FIG. 6, rotation of inner segment 54 as shown by arrow B serves to rotate gear 58 as shown by arrow C which in turn rotates end inner segment 54a as shown by arrow D, all as desired in accordance with the invention so as to provide twirling of tool head coupler 16 relative to body member 14.

Further, as desired, rotation of inner portion 48 relative to outer portion 46 is transmitted through joint 18 in accordance with the invention regardless of the angle of pivot of joint 18.

It should be noted that other types and/or configurations of gears and other structure for transmitting rotation of segments 54 of inner portion 48 across joints 18 could of course be utilized in accordance with the invention.

Figure 7:
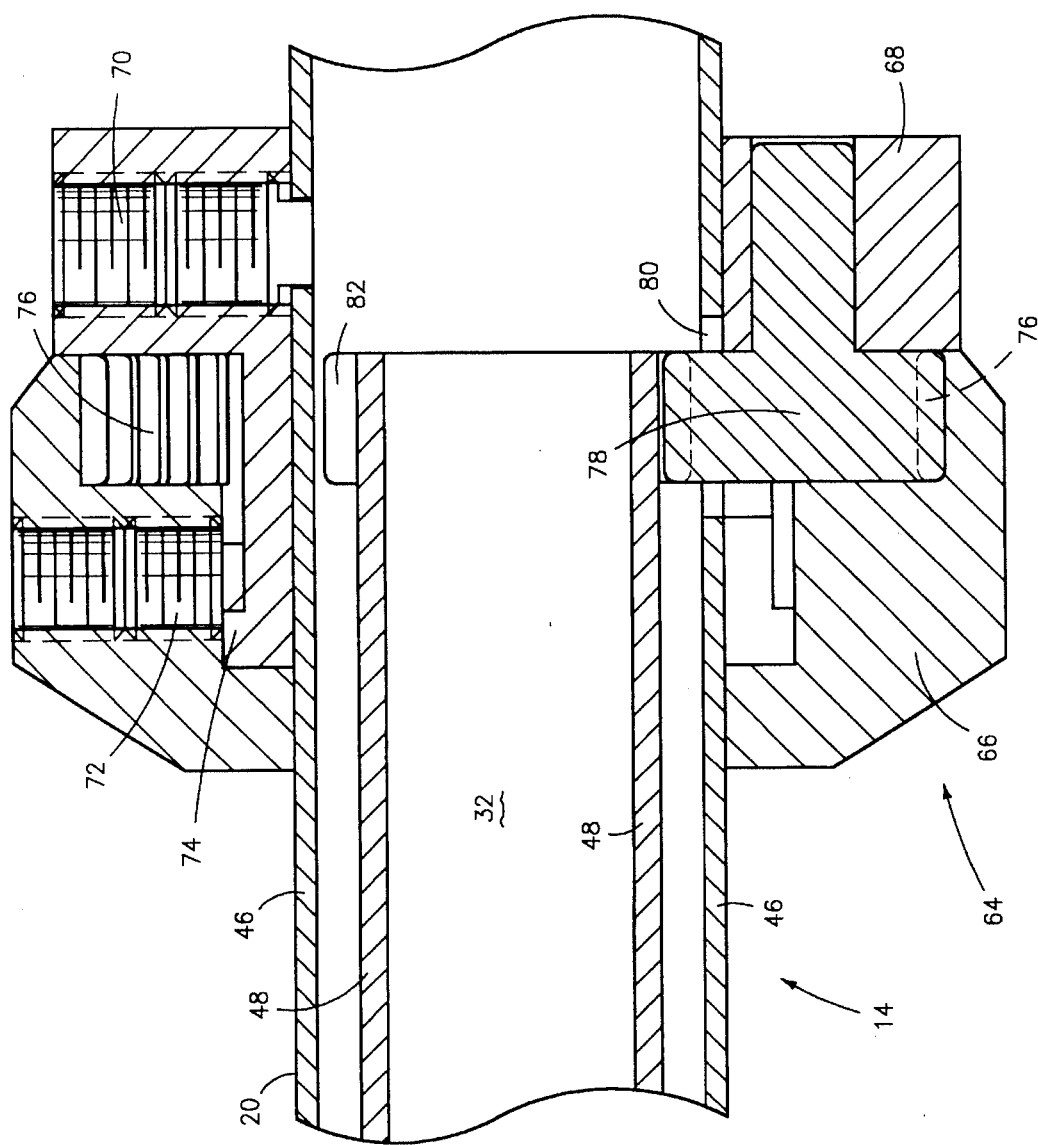
FIG. 7 is a sectional view of a twirling control member according to the invention.

Referring now to FIG. 7, a control member 64 for rotating inner portion 48 relative to outer portion 46 is shown. According to the invention, control member 64 preferably includes a collar 66 rotatably mounted around body member 14, preferably in close proximity to handle 12. Collar 66 may suitably be mounted over a bushing member 68 which is attached to outer tubular portion 46 for example by a set screw 70 as shown. An additional set screw 72 is preferably provided for holding collar 66 in place on bushing 68 and may abut against an extending ridge 74 protruding radially from bushing 68 as shown.

Collar 66 preferably has an internal gear surface 76 as shown in the drawing, and one or more spur gears 78 may preferably be rotatably positioned or mounted to bushing 68 in engagement with internal gear surface 76 of collar 66.

Outer tubular portion 46 preferably has a cutout area 80 arranged relative to bushing 68 and spur gear 78 so that the gear surface of spur gear 78 extends inwardly through cutout 80 to engage with a geared end 82 of inner tubular portion 48. Rotation of collar 66 serves to rotate spur gear 78 which in turn rotates inner portion 48 relative to outer portion 46 as desired. In this manner, control of rotation of inner portion 48 relative to outer portion 46, and thereby twirling of tool head coupler 16 relative to body member 14, is provided.

According to the invention, three spur gears 78 are preferably positioned substantially equally spaced around geared end 82 so as to provide desired stability of the control member 64. Of course, only a single spur gear 78 would suffice. Further, if a plurality of gears 78 are used, they are preferably but need not necessarily be equally spaced around geared end 82.

Referring to FIGS. 6 and 7, it should be noted that clockwise rotation of collar 66 of the shown embodiment would result in counter clockwise rotation of inner segment 54 which in turn would provide clockwise rotation of end inner segment 54a (FIG. 6) and the tool head attached thereto. With the illustrated configuration of control member 64, twirling of tool head coupler 16 will be in the same direction as rotation of collar 66 as long as an odd number of joints 18, preferably one or three, are provided. In an embodiment utilizing an even number of joints 18, rotation could be provided in the same direction, if desired, by placement of an additional spur gear (not shown) or through any other means which may be apparent to one skilled in the art.

As set forth above, body member 14 is also rotatable relative to handle 12. Referring back to FIG. 1, body member 14 is preferably mounted into a base member 83 which is rotatably received by handle 12. According to a preferred embodiment of the invention, base member 83 is rotatably and releasably held within a barrel portion 84 of handle 12. Base member 83 may preferably be coupled to handle 12 through a coupling structure such as that disclosed in co-pending and commonly owned U.S. patent application Ser. No. 08/055,639, filed Apr. 29, 1993. Other rotatable connections may of course be used in accordance with the invention. A releasable coupling is advantageous because the medical instrument is thereby easily disassembled for sterilization and the like and, furthermore, body members 14 of different length or diameter may be used with handle 12.

A portion of handle 12 is broken away in FIG. 1 to show a preferred coupling structure having a ridge 86 and groove 88 suitable for rotatable coupling or connection of base member 83 and handle 12. Rotation may thereby be provided, as shown by Arrow R, by simply rotating base member 83 relative to handle 12. Base member 83 may preferably be provided with a grip portion 90 or the like for facilitating such rotation.

Still referring to FIG. 1, it is noted that medical instrument 10 according to the invention further includes a member for operating a tool head 92 received by tool head coupler 16. According to the invention, tool head 92 is preferably operated through a push rod or member 94 slidably disposed within body member 14. Push rod 94 is connected or otherwise operatively associated with a trigger member 96 of handle 12 at one end as shown in the broken away portion of handle 12 in FIG. 1. As shown, end 98 of push rod 94 may suitably have an aperture 100 into which an end 102 of trigger 96 extends. The opposite or distal end 105 (FIG. 8) of push rod 94 extends into or is otherwise operatively associated with tool head coupler 16 to operate tool head 92 as desired. For example, if tool head 92 is a surgical stapler, sliding push rod 94 toward tool head 92 (Arrow X, FIG. 8) may serve to cock and fire a staple, while sliding push rod 94 toward handle 12 would ready tool head 92 (stapler) for the next stapling procedure, all as is well known in the art.

According to the invention, push rod 94 is preferably also pivotable at joint 18 to ensure proper operation of tool head 92 at the various positions to which it may be disposed. In this regard, push rod 94 in accordance with the invention must be pivotable along with joint 18 and longitudinally slidable when pivoted.

FIGS. 8 and 9 illustrate a push rod 94 according to the invention and adapted to pivot at joint 18. As shown, rod 94 is preferably a substantially elongate member slidably disposed within inner space 32 of body member 14. Rod 94 preferably includes a number of rod segments 104 connected by pivotable link elements 106. Rod 94 is preferably arranged within inner space 32 having a link element 106 substantially overlapping each joint 18. Pivotable connection of link element 106 to each adjacent segment 104 allows push rod 94 to be longitudinally displaced across joint 18 even when body member 14 is pivoted at joint 18.

Segments 104 according to the invention preferably terminate in a forked end 108 for supporting an axle 110 upon which link element 106 is pivotably supported. A roller member 112 is also preferably arranged on axle 110 and has a diameter or contour substantially matching the inside diameter and contour of body member 14. Roller 112 serves to provide smooth sliding of link elements 106 and push rod 94 at joint 18 as desired. As illustrated in the simplified cross section of FIG. 9, two laterally spaced link elements 106 positioned on axle 110 are preferably used to link adjacent rod segments 104 so as to provide enhanced stability of push rod 94. Rod segment 104a which corresponds to last segment 20a of body member 14 preferably terminates in end 105 which provides a contact surface for interacting with a tool received in coupler 16.

Link elements 106 are preferably provided according to the invention having a length sufficient to accommodate a range of desired longitudinal displacement of push rod 94 relative to body member 14 when body member 14 is pivoted. Link elements 106 also preferably have an inset or cut back edge 114 arranged facing the pivotally inner side 26 of body member 14. Cut back edge 114 serves to further accommodate sliding of push rod 94 and link element 106 relative to body member 14 when body member 14 is pivoted.

Push rod 94 as set forth above is preferably pivotable at locations corresponding to joints 18 in accordance with the invention. However, operation of the tool received in tool head coupler 16 may also be accomplished using a push rod 94 which is made of a flexible material, or which is rendered pivotable by other means.

Medical instrument 10 in accordance with the invention is useful with a wide variety of tool heads. According to the invention, last segment 20a terminates in a coupler mechanism which is preferably a releasable coupling mechanism such as that disclosed in co-pending U.S. patent application Ser. No. 08/055,639, mentioned above, and co-pending U.S. patent application Ser. No. 08/136,669 filed Oct. 15, 1993. Tool heads are thereby readily interchangeable and couplable with tool head coupler 16. Numerous types of tool heads such as, for example, staple cartridges, staple remover cartridges, surgical scissors, clamps, forceps, needle holders, graspers and the like are therefore readily interchangeable for use with medical instrument 10. Of course, tool head coupler 16 may instead be a permanent tool connection rather than a releasable connection if desired.

According to the invention, push rod 94 is readily removable from instrument 10 if desired so as to facilitate cleaning and sterilization of the device. Cleaning and sterilization, for example in an autoclave, is more effective with push rod 94 removed. Thus, in accordance with the invention, body member 14 may readily be disconnected from handle 12 and push rod 94 may be entirely removed from within body member 14 so as to provide enhanced sterilization.

It should be noted that medical instrument 10 in accordance with the invention provides pivot, twirl and rotation of the tool head attached to the body member as described above, thereby providing an extraordinarily versatile device. It should also be noted that any one or two of these features on their own or in combination likewise provides a useful and versatile apparatus in accordance with the invention.

Medical instrument 10 in accordance with the invention, when provided with three joint structures as shown in FIG.

1, provides an apparatus wherein the tool head can be pivoted up to a full 180 degrees and rotated and twirled at will. This allows numerous medical and surgical procedures to be performed through a cannula without requiring the relatively large incision which would conventionally be needed to access difficult portions of the body.

This invention may be embodied in other forms or carried out in other ways without departing from the spirit or essential characteristics thereof. The present embodiments are therefore to be considered as in all respects to be illustrative and not restrictive, the scope of the invention being indicated by the appended claims, and all changes which come within the meaning and range of equivalency are intended to be embraced therein.

What is claimed is:

1. A medical instrument, comprising:

a handle;

an elongate body member having a first end and a second end and at least one joint disposed therebetween dividing the body member into a plurality of segments including a first segment and a second segment, the first segment being connected to the handle and the second segment terminating in a tool head receiving means; and means for pivoting the second segment relative to the first segment at the at least one joint, wherein the means for pivoting comprises two elongate members fixed relative to the second segment of the body member, one positioned pivotally inside of the at least one joint and one positioned pivotally outside of the at least one joint, whereby tensioning the pivotally inside elongate member pivots the second segment toward a pivoted position, and whereby tensioning the pivotally outside elongate member pivots the second segment toward a straight position.

2. A medical instrument according to claim 1, wherein the means for pivoting further comprises a control member movably associated with the handle and having a cam surface, and wherein the at least one elongate member is engaged by the cam surface whereby movement of the control member relative to the handle selectively tensions and relaxes the at least one elongate member.

3. A medical instrument according to claim 2, wherein the at least one elongate member has a first end connected to the second segment and a second end connected to the control member.

4. A medical instrument according to claim 1, wherein the means for pivoting further comprises a control member movably associated with the handle and having a cam surface, and wherein the two elongate members are engaged by the cam surface whereby movement of the control member relative to the handle simultaneously tensions one and relaxes the other of the pivotally inner elongate member and the pivotally outer elongate member.

5. A medical instrument according to claim 4, wherein the control member is rotatably mounted to the handle and wherein the cam surface comprises a first cam segment having a first slope for engaging the pivotally inner elongate member and a second cam segment having a second slope for engaging the pivotally outer elongate member.

6. A medical instrument according to claim 5, wherein the first slope is substantially opposite to the second slope.

7. A medical instrument according to claim 1, wherein the two elongate members are disposed in tension in the body member whereby stability of the body member is enhanced.

8. A medical instrument according to claim 7, wherein the two elongate members are elastic.

9. A medical instrument according to claim 1, wherein the segments are pivotable at each joint of the at least one joint to an angle of between about 0° in a straight position and about 60° in a fully pivoted position.

10. A medical instrument according to claim 9, wherein the at least one joint comprises three joints disposed along the body member whereby the second segment is pivotable up to about 180° relative to the first segment in the fully pivoted position.

11. A medical instrument according to claim 1, wherein the body member is rotatably mounted to the handle.

12. A medical instrument, comprising:

a handle;

an elongate body member having a first end and a second end and at least one joint disposed therebetween dividing the body member into a plurality of segments including a first segment and a second segment, the first segment being connected to the handle and the second segment terminating in a tool head receiving means; and means associated with the handle for remotely rotating the tool head receiving means relative to the body member, wherein each segment of the first segment and the second segment comprises an inner portion and an outer portion, wherein the inner portion is rotatable relative to the outer portion, and wherein the tool head receiving means is positioned on the inner portion of the second segment.

13. A medical instrument according to claim 12, wherein the means for rotating comprises means for rotating the inner portion relative to the outer portion.

14. A medical instrument according to claim 12, further comprising means positioned at the at least one joint for transmitting rotation of the inner portion of the first segment to the inner portion of the second segment.

15. A medical instrument according to claim 14, wherein the inner portion has a geared end at at least one end thereof, and wherein the means for transmitting comprises at least one gear rotatably positioned at the at least one joint and engaging the geared end of adjacent inner portions whereby rotation of the inner portion of the first segment is transmitted across the at least one joint to the inner portion of the second segment.

16. A medical instrument according to claim 15, wherein the second segment is pivotable relative to the first segment at the at least one joint between a substantially straight position and a fully pivoted position, and wherein the at least one gear remains engaged with the geared end of adjacent inner portions when the second segment is pivoted between the substantially straight position and the fully pivoted position.

17. A medical instrument according to claim 15, wherein the at least one gear has an axis of rotation and the at least one joint has an axis of pivot which is co-linear with the axis of rotation whereby the at least one gear remains engaged with adjacent inner portions as the second segment is pivoted relative to the first segment.

18. A medical instrument according to claim 15, wherein the geared end of the inner portion comprises a plurality of gear teeth extending longitudinally from the at least one end for engaging the at least one gear.

19. A medical instrument according to claim 18, wherein the at least one gear has a first beveled surface and the geared end has a second beveled surface, and wherein the first beveled surface slopes so as to mesh with the second beveled surface.

20. A medical instrument according to claim 19, wherein the first beveled surface is beveled radially inwardly relative to the at least one gear so that a radius of the at least one gear increases as measured from an inner edge of the at least one gear to an outer edge of the at least one gear, and wherein the second beveled surface is beveled radially outwardly relative to the geared end so that the plurality of gear teeth shorten in length as measured from an inner surface of the geared end to an outer surface of the geared end.

21. A medical instrument according to claim 12, wherein the means for rotating comprises a control member rotatably positioned on one of the handle and the body member and associated with the inner portion of the first segment whereby rotation of the control member causes rotation of the inner portion of the first segment.

22. A medical instrument according to claim 21, wherein the control member comprises: a collar rotatably mounted to the handle and having an internal gear; at least one pinion gear mounted to the handle and engaging the internal gear; and a driven gear mounted on the inner portion of the first segment and engaged by the at least one pinion gear whereby rotation of the collar relative to the handle is transmitted to the inner portion of the first segment.

23. A medical instrument according to claim 12, wherein the body member is rotatably mounted to the handle.

24. A medical instrument, comprising:

a handle;

an elongate body member having a first end and a second end and at least one joint disposed therebetween dividing the body member into a plurality of segments including a first segment and a second segment, the first segment being connected to the handle and the second segment terminating in a tool head receiving means; and a push member longitudinally slidably disposed within the body member for operating a tool received by the tool head receiving means and including means for hinging the push member arranged substantially adjacent to the at least one joint whereby the push member is longitudinally slidable relative to the body member when the second segment is pivoted relative to the first segment, wherein the means for hinging comprise at least one link member positioned along the push member and overlapping the at least one joint, and wherein the length of the at least one link member is selected to provide a desired range of longitudinal sliding of the push member relative to the body member when the second segment is pivoted relative to the first segment.

25. A medical instrument according to claim 24, wherein the plurality of segments of the body member are substantially tubular and define therein a substantially continuous inner space, and wherein the push member is slidably disposed in the inner space.

26. A medical instrument according to claim 25, wherein the at least one link member positioned along the push member defines a plurality of push member segments each disposed within a respective segment of the body member, each link member having a length and two ends pivotably connected to adjacent push member segments whereby push member segments are pivotable relative to each other and the at least one link member.

27. A medical instrument according to claim 26, wherein the push member segments have at least one end terminating in a fork member supporting an axle, and wherein the axle pivotably supports an end of the at least one link member.

28. A medical instrument according to claim 27, wherein the hinge means further comprises a roller member supported on the axle and having an outside contour substantially corresponding to an inner contour of the body member.

29. A medical instrument according to claim 27, wherein the at least one link member comprises two link members at each joint of the body member, the two link members being laterally spaced on the axle whereby stability of the push member is enhanced.

30. A medical instrument according to claim 24, wherein the at least one joint has a pivotally inner side and a pivotally outer side and wherein the at least one link has a cutout portion facing the pivotally inner side for accommodating pivot at the at least one joint.

31. A medical instrument according to claim 24, wherein the push member has a first end associated with the handle and a second end associated with the tool head receiving means and further comprising a control member associated with the handle and the first end of the push member for longitudinally sliding the push member relative to the body member.

32. A medical instrument, comprising:

a handle;

an elongate body member having a first end and a second end and at least one joint disposed therebetween dividing the body member into a plurality of segments including a first segment and a second segment, the first segment being connected to the handle and the second segment terminating in a tool head receiving means;

means for pivoting the second segment relative to the first segment at the at least one joint;

means for rotating the tool head receiving means relative to the body member;

means for rotating the body member relative to the handle; and control means associated with the handle for controlling pivot of the plurality of segments of the body member, rotation of the body member relative to the handle, and rotation of the tool head receiving means relative tot he body member.

33. A medical instrument according to claim 32, wherein each segment of the body member comprises an inner portion and an outer portion, wherein the inner portion is rotatable relative to the outer portion, and wherein the tool head receiving means is positioned on the inner portion of the second segment, whereby the tool head receiving means is rotatable relative to the outer portion of the plurality of segments of the body member.

34. A medical instrument according to claim 33, further comprising a push member longitudinally slidably disposed within the inner portion of the plurality of segments of the body member and having a first end associated with the handle, a second end associated with the tool head receiving means, and means for hinging the push member arranged substantially adjacent to the at least one joint whereby the push member is pivotable with the body member and rotatable with the body member relative to the handle.

35. A medical instrument according to claim 34, wherein the inner portion of the plurality of segments of the body member is rotatable relative to the outer portion and the push member.

36. A medical instrument, comprising:

a handle;

an elongate body member having a first end and a second end and at least one joint disposed therebetween dividing the body member into a plurality of segments including a first segment and a second segment, the first segment being connected to the handle and the second segment terminating in a tool head receiving means, wherein the at least one joint comprises three joints disposed along the body member, and the segments are pivotable at each joint to an angle of between about 0° in a straight position and about 60° in a fully pivoted position, whereby the second segment is pivotable up to about 180° relative to the first segment in the fully pivoted position; and means for pivoting the second segment relative to the first segment at the at least one joint.

37. A medical instrument, comprising:

a handle;

an elongate body member having a first end and a second end and at least one joint disposed therebetween dividing the body member into a plurality of segments including a first segment and a second segment, the first segment being connected to the handle and the second segment terminating in a tool head receiving means; and means for pivoting the second segment relative to the first segment at the at least one joint, wherein the means for pivoting comprises at least one elongate member fixed relative to the second segment of the body member whereby longitudinal tensioning of the at least one elongate member pivots the second segment relative to the first segment at the at least one joint, wherein the means for pivoting further comprises a control member movably associated with the handle and having a cam surface, and wherein the at least one elongate member is engaged by the cam surface whereby movement of the control member relative to the handle selectively tensions and relaxes the at least one elongate member, wherein the at least one elongate member has a first end connected to the second segment and a second end connected to the control member.

38. A medical instrument, comprising:

a handle;

an elongate body member having a first end and a second end and at least one joint disposed therebetween dividing the body member into a plurality of segments including a first segment and a second segment, the first segment being connected to the handle and the second segment terminating in a tool head receiving means, wherein each segment of the first segment and the second segment comprises an inner portion and an outer portion, wherein the inner portion is rotatable relative to the outer portion, and wherein the tool head receiving means is positioned on the inner portion of the second segment; and means for rotating the tool head receiving means relative to the body member.

39. A medical instrument, comprising:

a handle;

an elongate body member having a first end and a second end and at least one joint disposed therebetween dividing the body member into a plurality of segments including a first segment and a second segment, the first segment being connected to the handle and the second segment terminating in a tool head receiving means;

means for pivoting the second segment relative to the first segment at the at least one joint; and a push member longitudinally slidably disposed within the body member for operating a tool received by the tool head receiving means and including means for hinging the push member arranged substantially adjacent to the at least one joint whereby the push member is longitudinally slidable relative to the body member when the second segment is pivoted relative to the first segment.

* * * * *